(12) United States Patent
Childress et al.

(10) Patent No.: US 7,060,849 B1
(45) Date of Patent: Jun. 13, 2006

(54) METHOD FOR PRODUCTION OF ISOCYANATOSILANES

(75) Inventors: R. Shawn Childress, Bartlesville, OK (US); Robert E. Sheridan, Marietta, OH (US); James L. McIntyre, Sistersville, WV (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/227,918

(22) Filed: Sep. 15, 2005

(51) Int. Cl.
*C07F 7/04* (2006.01)

(52) U.S. Cl. .................................................... 556/414
(58) Field of Classification Search ................ 556/414
See application file for complete search history.

(56) References Cited

U.S. PATENT DOCUMENTS

| | | | |
|---|---|---|---|
| 4,064,151 A | 12/1977 | Hedaya et al. | |
| 4,654,428 A | 3/1987 | Kurashima et al. | |
| 4,697,009 A | 9/1987 | Deschler et al. | |
| 5,218,133 A | 6/1993 | Pepe et al. | |
| 5,393,910 A | 2/1995 | Mui et al. | |
| 5,886,205 A | 3/1999 | Uchida et al. | |
| 6,008,396 A | 12/1999 | Sheridan et al. | |
| 6,388,117 B1 | 5/2002 | Pinske | |
| 6,673,954 B1 | 1/2004 | Gedon et al. | |
| 2004/0049064 A1 | 3/2004 | Kammel et al. | |
| 2004/0249179 A1 | 12/2004 | Kornek | |

FOREIGN PATENT DOCUMENTS

| | | |
|---|---|---|
| DE | 10108543 C1 | 4/2002 |
| DE | 10161272 A1 | 7/2002 |
| JP | 9208589 | 8/1997 |
| JP | 9328489 | 12/1997 |

*Primary Examiner*—Samuel Barts
(74) *Attorney, Agent, or Firm*—Dominick G. Vicari

(57) ABSTRACT

A process is provided for the production of isocyanatosilane from silylorganocarbamate by neutralizing the basic catalyst with an acid to provide an inert metal halide salt, and subjecting the reaction mixture to cracking reaction conditions to obtain isocyanatosilane.

31 Claims, 3 Drawing Sheets

METHOD FOR PRODUCTION OF ISOCYANATOSILANES

BACKGROUND OF THE INVENTION

This invention relates to economical and efficient process for making isocyanatosilanes.

Currently, all of the known methods for isocyanatosilanes production suffer from byproduct formation. The economics of isocyanatosilanes are highly dependant on the yield of product, thus, a process whereby the isocyanatosilane can be cleanly produced is highly sought. We have invented a process where the carbamatosilane is prepared in such a way that the byproduct salt is inert in nature and can be carried thru the cracking apparatus without generating heavy byproducts. In the past, the one preferred method of preparing acceptable carbamatosilane was to distill the feedstock prior to cracking. If the distillation was completed prior to cracking, impurities that could be detrimental to the cracking reaction were removed from the carbamate. With this invention, it can be shown that when a pot profile of the reaction mixture is analyzed during the cracking reaction, the profile of distilled and non-distilled are similar in appearance and the isocyanate lifetime is much improved from previously used non-distilled methods. With the improved lifetime of isocyanate, isolation of the isocyanate from the reactive zone will be easier to accomplish, and thus, the overall process will approach the performance observed with distilled feed.

A variety of processes are known for making isocyanatosilanes. Commercial synthesis of isocyanatosilanes is best demonstrated by the thermal cracking of the corresponding carbamatosilanes. In this process, the carbamate is subjected to high temperature under subatmospheric pressure. The patent literature teaches 3 basic procedures that involve thermal decomposition of carbamates:

1) cacking the neat carbamate;
2) utilization of inert media to assist in the cracking; and
3) vapor phase cracking using a hot tube cracker.

Thermal decomposition is the preferred method because it avoids the use of highly toxic and environmentally destructive phosgene. Due to the high reactivity of the isocyanate, all of these methods require that both the isocyanate and alcohol are quickly removed from the high temperature zone and then separated to prevent back addition of the alcohol. Although the isocyanate and alcohol separation can be routinely done by continuous fractional distillation while cracking, removing the reactive isocyanate from the cracking zone proves a challenge. Any isocyanate remaining in contact with the thermal medium will be further transformed into a range of non-desirable materials.

More recently, U.S. Pat. No. 6,388,117 teaches a continuous process that involves the addition of a tin catalyst prior to cracking in a cleavage and rectification unit. In this patent a portion of the material is routinely purged from the bottom of the cleavage reactor. Purging effectively serves two purposes: first, to maintain constant catalyst load; and second, to keep high molecular weight components at a constant level. The amount preferably removed from the bottom of the reactor is 15–25 percent by weight. This material is then allowed to mix with alcohol to quench the isocyanate, redistilled and partially fed back into the cracking zone.

U.S. Pat. Nos. 5,886,205 and 6,008,396 both teach a process where an inert solvent is used. These patents teach very similar methods except the former claims that pH control is required along with a transition metal catalyst. By utilizing the inert solvent, a large amount of waste is possible unless the high molecular weight material can easily be removed from the inert solvent. The economics would limit this type of separation.

High temperature vapor phase process is described in U.S. Pat. No. 5,393,910, DE 10064086 (U.S. Pat. Application Pub. No. 2004/0049064) and DE 10325608 (U.S. Pat. Application Pub. No. 2004/0249179). This vapor phase process suffers from the requirement of specialized equipment capable of high temperature operation, with the concurrent extensive capital investment. It is also reported in non-silyl isocyanate patents that coking of the reactor has hindered the commercialization of such units.

DE 10161272 describes a method where the carbamate is cracked in the presence of a high molecular weight isocyanate and transition metal catalyst. This process would likely suffer from heavies (i.e. nonvaporizable materials) isolation as the inert solvent patents described above do.

JP 9328489 teaches a method where the 3-aminopropylsilane is reacted first with isocyanate such as MDI to give the corresponding urea, which was then thermally cracked using catalytic conditions.

Other procedures are described that utilize a low temperature cracking of a carbamate derivative. For example, U.S. Pat. No. 4,697,009 describes a process where an acyl-urea group is utilized as the leaving group rather than alkyl alcohols that are most common. This process suffers from the intermediate preparation that involves difficult separation of solvent and the resulting salt.

U.S. Pat. No. 4,064,151 discloses the preparation of isocyanates by preparing halosilyl carbamates by direct reaction of aminosilane in the presence of $CO_2$ and halosilyl compounds, and a tertiary amine acid scavenger. The resulting halosilyl carbamate decomposes at a relatively low temperature to yield the isocyanate. However, a difficult workup is required to obtain the product of this process.

DE 10108543 describes a process where the carbamatosilane is reacted directly with methyl trichlorosilane to give the N-silylated carbamate, which then decomposes under slight heating to give the isocyanate and an equimolar amount of alkoxychloromethylsilane. This method suffers from the requirement of an acid trap such as triethylamine, which then requires separation and disposal or recycle.

Typical of non-cracking methods are found in JP 09208589 and U.S. Pat. No. 4,654,428 in which the aminopropylsilane is directly reacted with highly toxic phosgene to yield the desired isocyanate.

In the current literature, the starting carbamatosilane is prepared by multiple processes. U.S. Pat. No. 6,388,117 teaches the preparation of carbamatoorganosilane by the reaction of aminoorganosilane, urea, and alcohol to form the carbamatoorganosilane. This distillation is claimed to be an important part of the process to obtain carbamatoorganosilanes and the corresponding isocyanatosilane.

U.S. Pat. No. 5,218,133 describes the preferred synthesis of carbamatosilane by reacting aminosilane with dialkylcarbonates in the presence of a strong base such as sodium methoxide. The residual sodium methoxide is then neutralized with a carboxylic acid. Although this carbamatosilane is then used to prepare silylisocyanurates in the presence of transition metal catalysts, U.S. Pat. No. 5,393,910 describes this method to be the preferred for the preparation of carbamatosilanes used in the manufacture of isocyanatosilanes via gas phase pyrolysis. No mention of distillation is noted in this patent.

SUMMARY OF THE INVENTION

A process for preparing an isocyanatosilane which comprises: a) providing a mixture of silyorganocarbamate and metal alkoxide catalyst employed in obtaining the silylorganocarbamate; b) neutralizing the metal alkoxide compound of said mixture with halogen-containing neutralizing agent to provide a mixture of silylorganocarbamate and metal salt; and c) subjecting the mixture of silylorganocarbamate and metal salt to cracking conditions to provide isocyanatosilane.

The process of the invention can provide a near quantitative yield of isocyanatosilane, which is an industrially important product, thereby greatly reducing or eliminating the expense of distillation associated with known processes for making isocyanatosilane. Important advantages of neutralizing the metal alkoxide catalyst compound with halogen-containing neutralizing prior to cracking are higher yields, extended reaction time, and increased purity of the obtained isocyanatosilanes.

DETAILED DESCRIPTION OF THE INVENTION

Figure 1:
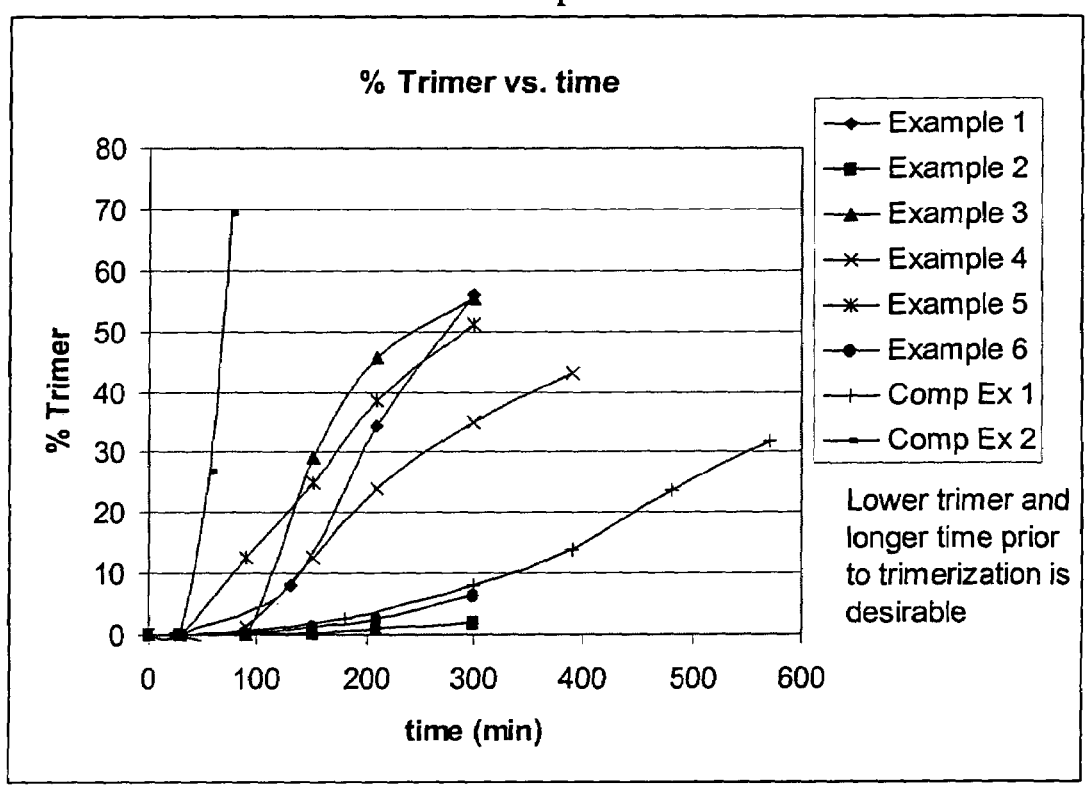
FIG. 1 is a graph (1), which illustrates the time required for isocyanurate trimer to form.

It is known that in the reaction leading to silylisocyanurate, the carbamotosilane must first crack to give the isocyanatosilane intermediate, which then if kept in contact with the reaction medium for extended time, trimerizes to give the silylisocyanurate. Therefore, if one desires the isocyanatosilane it is advantageous to quickly remove the isocyanatosilane from the reaction medium. In reality, this is a large challenge due to the quick trimerization reaction. Silylisocyanurate reaction chemistry follows:

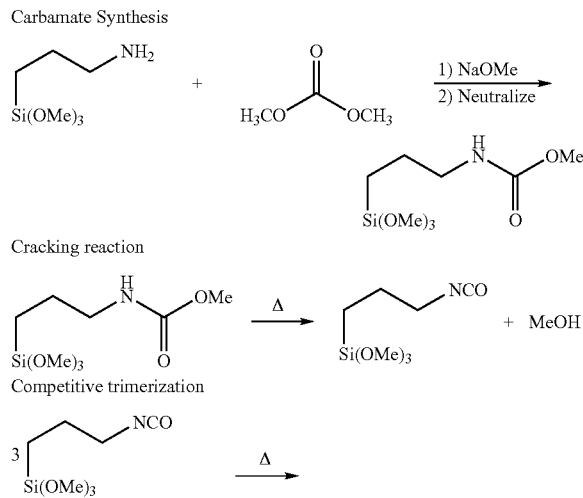

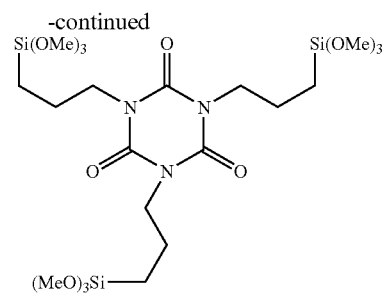

One way to extend the lifetime of isocyanatosilane, so that its removal may be possible, is to remove any active trimerization catalyst from the system. Distillation serves as a very good means to accomplish this. Other removal methods may also be incorporated but are not described at this time. Although trimerization catalysts, such as carboxylate salts, are present in the carbamate feed described in U.S. Pat. No. 5,218,133, it should be noted that other catalysts may be possible.

Since distillation proves to be an expensive commercial operation, chemical means of extending the isocyanato lifetime have been sought. We have discovered that an effective solution to this challenge is the neutralization of the metal alkoxide with a neutralizing agent that provides an inert salt that can be carried thru the cracking reaction without detrimental effects on the isocyanatosilane (i.e. trimerization).

Carbamates to be used for the feedstock of the present invention can be prepared by any known methods. However, the preferred method is described in U.S. Pat. Nos. 5,218,133 and 6,673,954, the entire contents of which are incorporated by reference. In one embodiment of the present invention, the corresponding aminopropylsilane is reacted with dialkylcarbonate in the presence of sodium methoxide catalyst. Other suitable bases for this process include the metal alcoholates. Examples of which include, but are not limited to sodium methoxide, sodium ethoxide, calcium methoxide, calcium ethoxide, sodium propoxide, sodium t-butoxide, potassium methoxide, potassium ethoxide, potassium propoxide, potassium t-butoxide, lithium methoxide, lithium ethoxide, lithium propoxide, and lithium t-butoxide, and the like.

Carbamates that are represented by this process have the formula:

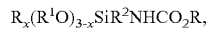

wherein x is an integer having a value of 0, 1, 2, or 3. Each R separately represents an alkyl group or halogenated alkyl group of 1 to 12 carbon atoms, a cycloalkyl group or halogenated cycloalkyl group of 5 to 8 carbons, an aryl group of 6 to 14 carbons or an alkaryl or aralkyl group of 7 to 15 carbons. Each $R^1$ is separately R or a silyl $R_3Si-$, or a siloxy group $R_3Si(OSiR_2)_m$—wherein m is an integer having a value of 1 to 4, or when x is 0 or 1 two $R^1$ groups taken together may forma a divalent siloxy group $-R_2(OSiR_2)_n$—wherein n is an integer having a value of 3, 4, or 5 thus forming a cyclic silxane with the silicon atom bearing the carbamatosilane group. $R^2$ represents a linear or branched divalent saturated or unsaturated hydrocarbon group of 1 to 20 carbons attached to silicon by a silicon-carbon bond; and wherein R, $R^1$ and $R^2$ optionally may contain heteroatom functional groups such as ether, thioether, sulfone, ketone, ester, amide, nitrile, or halogen.

The previous teachings neutralize with acetic acid after carbamate synthesis; however, in one embodiment of the present invention the neutralizing agent is one other than carboxylic acid, such that upon neutralization an inert metal halide salt, such as sodium chloride, results.

As described herein, neutralization utilizing reactive acidic halides, such as, ammonium halides, carboxylic acid halides and the like, to give the corresponding metal halide are disclosed. To illustrate the procedure, the neutralization was chosen such that the resulting neutralization salt is sodium chloride; however, other halide salts can be utilized.

Suitable neutralizing agents include, but are not limited to reactive acidic halides, such as, ammonium halides, carboxylic acid halides and the like, to give the corresponding metal halide salt. In one embodiment of the present invention ionic neutralizing agents are used. Suitable ionic neutralizing agents include, but are not limited to, materials such as ammonium chloride, dimethyl ammonium chloride, diethylammonium chloride and the like. In another embodiment of the present invention, the ionic neutralization agent is ammonium chloride. Further, the ionic neutralizing agents, as contemplated herein, can be extended to the entire halide family.

One advantage to utilizing the ammonium halide salts to neutralize the carbamate is that the resulting amine can easily be stripped from the reaction mixture prior to cracking. This stripping step, which is required anyway, removes the amine, which could possibly lead to byproduct formation during cracking. To allow ease of stripping these amines, the smaller homologues for the amine salts are preferred.

In another embodiment of the present invention suitable nonionic neutralizing agents are used. Suitable nonionic neutralization species include, but are not limited to, materials such as acetyl chloride, propionyl chloride, butyryl chloride and the like. In another embodiment of the present invention, the nonionic neutralizing agent is propionyl chloride. The acyl chlorides have an advantage of generating esters upon reaction with the basic catalyst. These esters can either be stripped prior to the cracking reaction or if not detrimental to the cracking reaction or final product can be carried thru the process.

In an alternative embodiment of the present invention, chlorosilanes, phosphrous chlorides and other reactive organohalides can be utilized as neutralizing agents. Such materials would include, but are not limited to methyltrichlorosilane, dichlorodimethylsilane, chlorotrimethylsilane, propyltrichlorosilane, phosphrous oxychloride, phosphorous trichloride, benzylchloride, methylchloride, and the like.

The amount of neutralizing agent is based on equivalent weights of the metal alkoxide catalyst employed in obtaining the silylorganocarbamate. The amount of neutralizing agent is from about 0.75 equivalents to about 2 equivalents in respect to the contained alkoxide of the metal alkoxide catalyst with the most preferred from about 1 to about 1.5 equivalents. The desire is to effectively neutralize any basic-metal alkoxide catalyst in the mixture.

In one embodiment of the present invention, the neutralization is carried out to a pH of about 3 to about 10. In another embodiment of the present invention, the neutralization is carried out to a pH from about 4 to about 7 prior to cracking the carbamatosilane. In yet another embodiment of the present invention, if the pH is not within the desired range, an acid other than the neutralizing agent, can be added to the mixture after the material has been fully neutralized with an equivalent amount of neutralizing agent. If utilizing the ammonium salts, this acid is added preferably after the material has been stripped of residual ammonia or alkyl amines in order to prevent the formation of ammonium salts of the acid. In still another embodiment of the present invention, acetic acid can be added if the pH is not within the desired range, but it should be understood that various homologues are capable of providing the same results. Other examples of non-carboxylic acids that may effectively acidify the mixture after neutralization include, but are not limited to, polyphosphoric acid, superphosphoric acid, and hydrochloric acid, and the like.

Prior to the cracking process, it is desirable to remove any residual solid materials that result from the process. These solids may contain remnants of the carbamatosilane reaction and/or salts due to neutralization. It is anticipated that these solids may have a detrimental effect on the cracking process by depositing on mechanical equipment, and thus, resulting in mechanical failure. It is also possible that a buildup of these solids may lead to competitive side reactions.

When solid salts such as ammonium chloride are utilized as neutralizing agents it is preferred that they are first dissolved in a suitable solvent prior to addition to the carbamate. The solvent of choice for this procedure is the same alcohol as the alkoxy groups on the silane. Methanol, for example, would be preferred for methoxysilane carbamates where as ethanol would be preferred for ethoxysilane carbamates. Alternatively, the solvent should be chosen so there is limited transesterification on the silane during the neutralization. Suitable solvents include, but are not limited to, aromatic solvents such as toluene, xylene, chlorobenzene, dichlorobenzene, hydrocarbon solvents such as pentane, hexane, heptane or octane, ether solvents such as diethylether, diisopropylether, 1,4-dioxane, tetrahydrofuran, or the various glymes, organic esters such as methylacetate or ethylacetate, chlorinated hydrocarbons such as dichloromethane, 1,2-dichloroethane, or carbon tetrachloride, nitrile solvents such as acetonitrile, propionitrile, and the like.

The isocyanatosilanes of the present invention are represented by the following formula:

$R_x(R^1O)_{3-x}SiR^2NCO$, wherein x is an integer having a value of 0, 1, 2, or 3. Each R separately represents an alkyl group or halogenated alkyl group of 1 to 12 carbon atoms, a cycloalkyl group or halogenated cycloalkyl group of 5 to 8 carbons, an aryl group of 6 to 14 carbons or an alkaryl or aralkyl group of 7 to 15 carbons. Each $R^1$ is separately R or a silyl $R_3Si-$, or a siloxy group $R_3Si(OSiR_2)_m$—wherein m is an integer having a value of 1 to 4, or when x is 0 or 1 two $R^1$ groups taken together may forma a divalent siloxy group $-R_2(OSiR_2)_n$—wherein n is an integer having a value of 3, 4, or 5 thus forming a cyclic silxane with the silicon atom bearing the carbamatosilane group. $R^2$ represents a linear or branched divalent saturated or unsaturated hydrocarbon group of 1 to 20 carbons attached to silicon by a silicon-carbon bond; and wherein R, $R^1$ and $R^2$ optionally may contain heteroatom functional groups such as ether, thioether, sulfone, ketone, ester, amide, nitrile, or halogen.

Illustrative of isocyanatosilane produced in the neutralization reaction step are 3-isocyanatopropyltrimethoxysilane, isocyanatopropylmethyl-dimethoxysilane, isocyanatobutyltrimethoxysilane, isocyanatobutylmethyl-dimethoxysilane, isocyanatopropyltriethoxysilane, isocyanatopropylethyldiethoxysilane, isocyanatopropyldimethylmethoxysilane, isocyanatopropylmethoxydiethoxysilane, isocyanatobutyltriethoxysilane, isocyanatopropylphenylmethylmethoxysilane, and the like.

EXAMPLES

The following examples are illustrative of the process of the invention. The general procedure for neutralization of Examples 1 through 6, and comparative Examples 1 and 2, and determination of pot profile during cracking reaction of Examples 7 follow:

To a 2 L 4 necked round bottom flask equipped with overhead stirrer, Vigreux column, thermocouple, and distillation head was added commercially prepared methyl N-3-(trimethoxysilyl)propylcarbamate reaction mixture prepared by the method described in U.S. Pat. No. 5,218,533. This mixture, which contained sodium methoxide, was treated with the neutralization species as provided in TABLE 1, and mechanically stirred. After neutralization, a portion of acetic acid was optionally added to adjust the pH to the desired range. The lites fraction was then stripped and the resulting mixture was filtered thru a 1–5 micron pad prior to the cracking reaction.

TABLE 1

| | Neutralizing Acid | ppm | Additional Acid | ppm | Final pH |
|---|---|---|---|---|---|
| Example 1 | ammonium Chloride | 3,400 | | | 7.14 |
| Example 2 | ammonium Chloride | 3,400 | Acetic acid | 2,800 | 4.66 |
| Example 3 | dimethylamine - HCl | 3,900 | | | 6.11 |
| Example 4 | dimethylamine - HCl | 5,250 | Acetic acid | 367 | 6.28 |
| Example 5 | propionyl chloride | 3,850 | | | 3.01 |
| Example 6 | propionyl chloride | 700 | Acetic Acid | 1,670 | 5.83 |
| Comparative Example 1 | distilled feed | | | | NA |
| Comparative Example 2 | acetic acid | ~6,700 | | | 6.19 |

Definitions and Analysis:

The measurements that best describe the reaction profile are the percent trimerization, and percent isocyanatosilane. The term "percent trimerization" as understood herein, is the percentage of silylisocyanurate mass present in the mixture. The term "percent isocyanatosilane" as understood herein, is the percentage isocyanatosilane mass present in the mixture.

For a successful reaction, the outcome would be one where the percent trimer is minimized and the isocyanatosilane is present in a relatively large amount. This indicates that the medium in which the cracking occurs is not favorable for byproduct formation resulting from combination of the isocyanatosilane, and thus, isolation of the isocyanatosilane will be possible. The graphical representations of FIGS. 1 and 2 best describe the outcome of the experiments.

Figure 2:
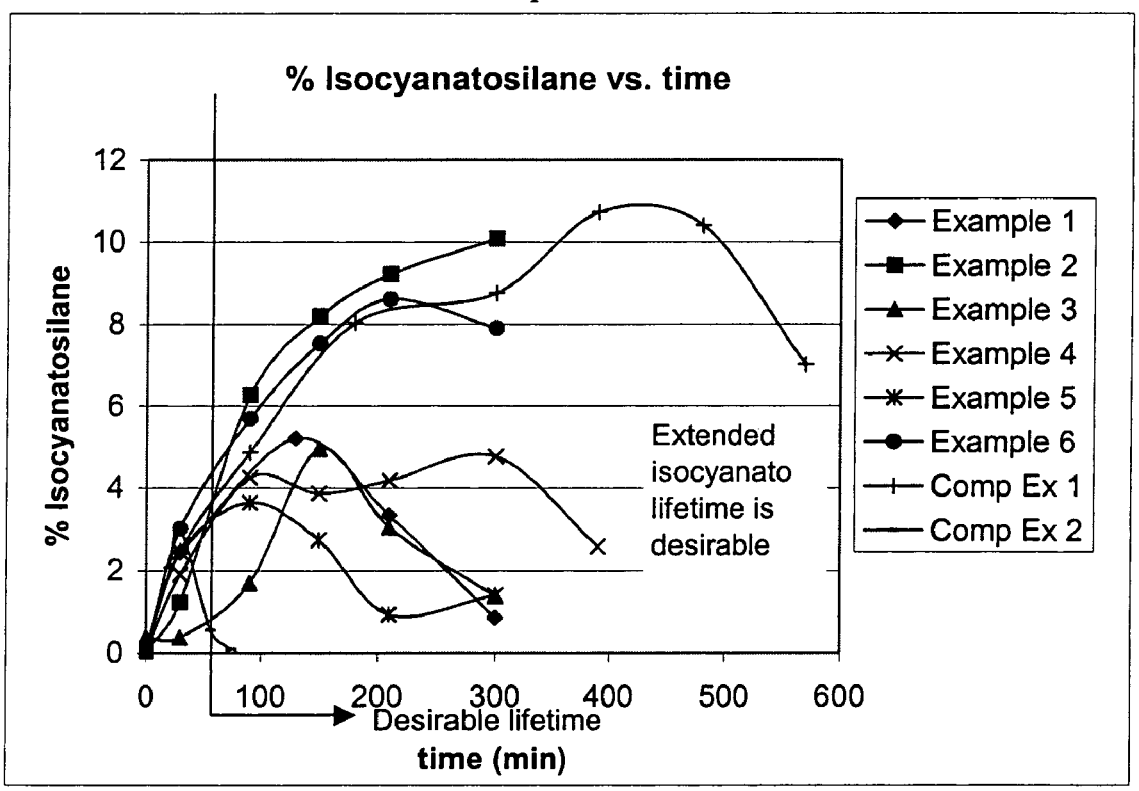
FIG. 2 is a graph (2), which illustrates the isocyanatosilane extended lifetime.

The graphs in FIGS. 1 and 2 illustrate the improved reaction when the carbamatosilane mixture is neutralized with non-carboxylic acid agents. The two controls that are used for comparison are distilled carbamatosilane (Comparative Example 1) and acetic acid neutralized carbamatosilane (Comparative Example 2). The desirable profile would be the distilled material. It can be seen when the distilled feed is used, the isocyanurate trimer is slow to form (FIG. 1); and the isocyanatosilane has a relatively long lifetime (FIG. 2). On the other hand, if acetic acid is used for the neutralization the trimer forms very rapidly (see FIG. 1) with consumption of the isocyanatosilane. The complete reaction occurs within 1 hour of reaction time. This quick conversion of isocyanatosilane to trimer would make the isolation of isocyanatosilane very difficult in commercial equipment. When neutralized with non-carboxylic agents as described herein, the lifetime of the reactive isocyanatosilane approaches that of the distilled feed, which is highly desirable.

EXAMPLE 7

This example illustrates the isolation of isocyanatosilane from the reaction zone. To 1,500 grams of commercially prepared methyl N-3-(trimethoxysilyl)propylcarbamate containing sodium methoxide was added 193 grams of a 3.13 weight percent solution of $NH_4Cl$ in methanol. This mixture was stirred for 2 hrs. The resulting solvent pH was 8.95. The lites were then vacuum stripped during which time the pH further dropped to 5.33. To this mixture, 3.4 grams of acetic acid was charged to adjust the pH to 4.63 and the mixture was filtered thru a 5 micron pad.

To crack the resulting carbamate, 1,090 grams of the neutralized and filtered material was added to a 2 Liter round bottom flask equipped with mechanical agitator, stainless steel packed column, simple distillation head, partial condenser set at 60° C., and receiver. The reaction conditions were then set to 210° C. and 100 mmHg. The valve on the distillation head was pinched just enough to return reflux back to the column until a desired head temperature was reached that indicates high purity 3-isocyanatopropyltrimethoxysilane. These conditions were held for 5.5 hrs. The following analytical results in TABLES 2 and 3 were obtained from Example 7:

To measure the pot profile during the cracking reaction, the mixture was then rapidly heated to 210° C. with initial pressure set at 300 mmHg. The temperature was held around 210° C. and the pressure set to remove only the resulting alcohol. The reaction profile was tested via gas chromatography over multiple hours by periodic removal and testing of an aliquot from the reaction zone.

TABLE 2

Receiver - Recovered 645 grams

| Time (min) | Carbamate (%) | Isocyanate (%) | Trimer (%) |
|---|---|---|---|
| 99 | 22.35 | 68.95 | 0 |
| 159 | 4.44 | 94.86 | 0 |
| 219 | 4.51 | 94.82 | 0 |
| 279 | 5.46 | 93.74 | 0 |
| 339 | 24.04 | 74.86 | 0 |

TABLE 3

Reaction Pot - Recovered 310 grams

| Time (min) | Carbamate (%) | Isocyanate (%) | Trimer (%) |
|---|---|---|---|
| 99 | 93.55 | 1.77 | 0 |
| 159 | 88.75 | 1.64 | 0 |
| 219 | 81.67 | 1.84 | 0 |
| 279 | 73.46 | 2.08 | 3.35 |
| 339 | 69.26 | 2.05 | 7.77 |

Figure 3:
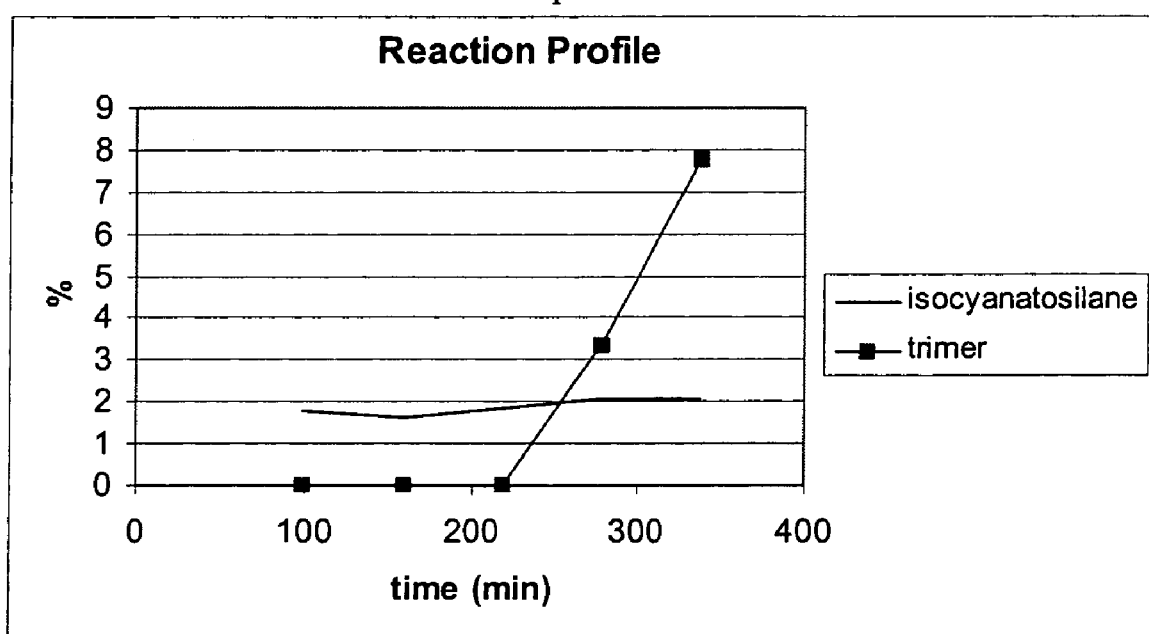
FIG. 3 is a graph (3), which illustrates the reaction profile of isocyanatosilane and trimer.

Results of high purity isocyanatosilane recovered in high yields coupled with the reaction profile as illustrated in the graph of FIG. 3, which shows only small amounts of isocyanatosilane remain in reaction zone, clearly demonstrates that this method is a alternative process to for the preparation of isocyanatosilanes without distillation.

What is claimed is:

1. A process for preparing an isocyanatosilane which comprises:
   a) providing a mixture of silyorganocarbamate and metal alkoxide catalyst employed in obtaining the silylorganocarbamate;
   b) neutralizing the metal alkoxide compound of said mixture with halogen-containing neutralizing agent to provide a mixture of silylorganocarbamate and metal salt; and
   c) subjecting the mixture of silylorganocarbamate and metal salt to cracking conditions to provide isocyanatosilane.

2. The process of claim 1, wherein the silylorganocarbamate is of the general formula $$R_x(R^1O)_{3-x}SiR^2NHCO_2R$$

wherein x is an integer having a value of 0, 1, 2, or 3, R represents an alkyl group or halogenated alkyl group of 1 to 12 carbon atoms, a cycloalkyl group or halogenated cycloalkyl group of 5 to 8 carbons, an aryl group of 6 to 14 carbons or an alkaryl or aralkyl group of 7 to 15 carbons, $R^1$ is separately R or a silyl $R_3Si$, or a siloxy group $R_3Si(OSiR_2)_m$ wherein m is an integer having a value of 1 to 4, or when x is 0 or 1 two $R^1$ groups taken together may form a divalent siloxy group $R_2(OSiR_2)_n$ wherein n is an integer having a value of 3, 4, or 5 forming a cyclic silxane with the silicon atom bearing the carbamatosilane group, $R^2$ represents a linear or branched divalent saturated or unsaturated hydrocarbon group of 1 to 20 carbons attached to silicon by a silicon-carbon bond, and wherein R, $R^1$ and $R^2$ optionally may contain heteroatom functional groups such as ether, thioether, sulfone, ketone, ester, amide, nitrile, or halogen.

3. The process of claim 1, wherein the isocyanatosilane is of the general formula $$R_x(R^1O)_{3-x}SiR^2NCO$$

wherein x is an integer having a value of 0, 1, 2, or 3, R separately represents an alkyl group or halogenated alkyl group of 1 to 12 carbon atoms, a cycloalkyl group or halogenated cycloalkyl group of 5 to 8 carbons, an aryl group of 6 to 14 carbons or an alkaryl or aralkyl group of 7 to 15 carbons, $R^1$ is separately R or a silyl $R_3Si$—, or a siloxy group $R_3Si(OSiR_2)_m$, wherein m is an integer having a value of 1 to 4, or when x is 0 or 1 two $R^1$ groups taken together may form a divalent siloxy group $R_2(OSiR_2)_n$, wherein n is an integer having a value of 3, 4, or 5 forming a cyclic silxane with the silicon atom bearing the carbamatosilane group, $R^2$ represents a linear or branched divalent saturated or unsaturated hydrocarbon group of 1 to 20 carbons attached to silicon by a silicon-carbon bond, and wherein R, $R^1$ and $R^2$ optionally may contain heteroatom functional groups such as ether, thioether, sulfone, ketone, ester, amide, nitrile, or halogen.

4. The process of claim 2, wherein the silylorganocarbamate is at least one of methyl N-3-(trimethoxysilyl)-propylcarbamate, ethyl N-3-(trimethoxysilyl) propylcarbamate, methyl N-3-(triethoxysilyl)propylcarbamate, methyl N-3-(methyldimethoxysilyl)-propylcarbamate, methyl N-3-(dimethylmethoxysilyl)-propylcarbamate, methyl N-3-(triethoxysilyl) propylcarbamate, ethyl N-3-(triethoxysilyl)-propylcarbamate, methyl N-3-(methoxydiethoxysilyl)propylcarbamate, methyl N-3-(trimethoxysilyl) butylcarbamate and methyl N-3-(triethoxysilyl)-butylcarbamate, the isocyanatosilane is at least one of 3-isocyanato propyltrimethoxysilane, 3-isocyanatopropylmethyldimethoxysilane, isocyanatobutyltrimethoxysilane, isocyanatobutylmethyldimethoxysilane, 3-isocyanatopropyltriethoxysilane, isocyanatopropylethyldiethoxysilane, isocyanatopropyldimethylmethoxysilane, isocyanatopropylmethoxydiethoxysilane, isocyanatobutyltriethoxysilane and isocyanatopropylphenylmethylmethoxysilane and the silyisocyanurate is at least one of 1,3,5-tris(trimethoxysilylpropyl)isocyanurate, 1,3,5tris(methyldimethoxysilylpropyl)isocyanurate, 1,3,5-tris(trimethoxysilylbutyl) isocyanurate, 1,3,5-tris(methyldimethoxysilylbutyl)isocyanurate, 1,3,5-tris (triethoxysilylpropyl)isocyanurate and 1,3,5-tris (phenylmethylmethoxysilylpropyl)isocyanurate.

5. The process of claim 1, wherein the halogen-containing neutralizing agent is an acyl halide.

6. The process of claim 1, wherein the halogen-containing neutralizing agent is selected from the group consisting of akyl halides, aryl halides, ammonium halides, carboxylic acid halides, and mixture thereof.

7. The process of claim 6, wherein the halogen-containing neutralizing agent is selected from the group consisting of acetyl chloride, ammonium chloride, propionyl chloride, butyryl chloride, dimethyl ammonium chloride, diethylammonium chloride and mixtures thereof.

8. The process of claim 1, wherein the halogen-containing neutralizing agent is selected from the group consisting of chlorosilanes, phosphrous chlorides, and mixtures thereof.

9. The process of claim 1, wherein the resulting amine is stripped from the reaction mixture prior to cracking.

10. The process of claim 1, wherein the halogen-containing neutralizing agent is based on equivalent weights of the contained alkoxide of the metal alkoxide catalyst.

11. The process of claim 10, wherein the amount of halogen-containing neutralizing agent is from about 0.75 equivalents to about 2 equivalents with respect to the contained alkoxide of the metal alkoxide catalyst.

12. The process of claim 11, wherein the amount of halogen-containing neutralizing agent is from about 1 to about 1.5 equivalents with respect to the contained alkoxide of the metal alkoxide catalyst.

13. The process of claim 1, wherein neutralization is carried out to a pH of about 3 to about 10 prior to cracking the carbamatosilane.

14. The process of claim 13, wherein neutralization is carried out to a pH of about 4 to about 7 prior to cracking conditions to provide isocyanatosilane.

15. The process of claim 14, wherein an acid is added in addition to the halogen-containing neutralizing agent.

16. The process of claim 15, wherein the acid is selected from the group consisting of polyphosphoric acid, superphosphoric acid, and hydrochloric acid.

17. The process of claim 15, wherein the acid is a carboxylic acid.

18. The process of claim 15, wherein the acid is acetic acid.

19. The process of claim 1, further comprising removal of residual solid material prior to cracking conditions to provide isocyanatosilane.

20. The process of claim 5, wherein the halogen-containing neutralizing agent is dissolved in suitable a solvent.

21. The process of claim 20, wherein the solvent is selected from the group consisting of alcohols, aromatic solvents, ether solvents, and mixtures thereof.

22. The process of claim 1, wherein the purity of the isocyanatosilane is greater than isocyanatosilane obtained when metal alkoxide catalyst is not neutralized with said halogen-containing neutralizing agent.

23. The process of claim 7, wherein the neutralizing agent is propionyl chloride.

24. The process of claim 8, wherein the neutralizing agent is selected from the group consisting of methyltrichlorosilane, dichlorodimethylsilane, chlorotrimethylsilane, propyltrichlorosilane, phosphrous oxychloride, phosphorous trichloride, methylchloride benzylchloride, and mixtures thereof.

25. The process of claim 21, wherein the alcohol solvent is selected from the group consisting of methanol, ethanol, and mixtures thereof.

26. The process of claim 21, wherein the aromatic solvent is selected from the group consisting of toluene, xylene, and mixtures thereof.

27. The process of claim 21, wherein the ether solvent is selected from the group consisting of diethylether, tetrahydrofuran, diisopropylether, 1,4-dioxane, diglyme and triglyme, and mixtures thereof.

28. The process of claim 21, wherein the ester solvent is selected from methyl acetate, ethyl acetate, and mixtures thereof.

29. The process of claim 21, wherein the chlorinated hydrocarbon solvent is selected from dichloromethane, carbon tetrachloride, 1,2-dichloroethane, chloroform, chlorobenzene, dichlorobenzene and mixtures thereof.

30. The process of claim 21, wherein the nitrile solvent is acetonitrile, propionitrile, and mixtures thereof.

31. The process of claim 1, wherein the metal alkoxide catalyst is selected from the group consisting of sodium methoxide, sodium ethoxide, calcium methoxide, calcium ethoxide, sodium propoxide, sodium t-butoxide, potassium methoxide, potassium ethoxide, potassium propoxide, potassium t-butoxide, lithium methoxide, lithium ethoxide, lithium propoxide, and lithium t-butoxide, and mixture thereof.

* * * * *